United States Patent [19]

Chu et al.

[11] Patent Number: 5,767,122
[45] Date of Patent: Jun. 16, 1998

[54] ENANTIOMERICALLY PURE β-D-DIOXOLANE NUCLEOSIDES

[75] Inventors: Chung K. Chu, Athens; Raymond F. Schinazi, Decatur, both of Ga.

[73] Assignees: Emory University, Atlanta; The University of Georgia Research Foundation, Inc., Athens, both of Ga.

[21] Appl. No.: 469,465

[22] Filed: Jun. 6, 1995

Related U.S. Application Data

[60] Division of Ser. No. 935,515, Aug. 25, 1992, which is a continuation-in-part of Ser. No. 622,762, Dec. 5, 1990, Pat. No. 5,179,104.

[51] Int. Cl.$^6$ .................... C07D 473/00; A61K 31/505
[52] U.S. Cl. .................... 514/262; 544/276; 544/277
[58] Field of Search .................... 544/276, 277; 514/262

[56] References Cited

U.S. PATENT DOCUMENTS

| | | | |
|---|---|---|---|
| 4,000,137 | 12/1976 | Dvonoch et al. | 260/252 |
| 4,336,381 | 6/1982 | Nagata et al. | 544/313 |
| 4,861,759 | 8/1989 | Mitsuya et al. | 514/46 |
| 4,879,277 | 11/1989 | Mitsuya et al. | 514/49 |
| 4,880,784 | 11/1989 | Robins et al. | 514/48 |
| 4,916,122 | 4/1990 | Chu et al. | 514/50 |
| 4,963,533 | 10/1990 | de Clerq et al. | 514/49 |
| 5,011,774 | 4/1991 | Farina | 435/87 |
| 5,041,449 | 8/1991 | Belleau et al. | 514/274 |
| 5,047,407 | 9/1991 | Belleau et al. | 514/274 |
| 5,059,690 | 10/1991 | Zahler et al. | 544/276 |
| 5,071,983 | 12/1991 | Koszalka et al. | 544/317 |
| 5,122,517 | 6/1992 | Vince et al. | 514/50 |
| 5,179,104 | 1/1993 | Chu et al. | 544/310 |
| 5,204,466 | 4/1993 | Liotta et al. | 544/317 |
| 5,210,085 | 5/1993 | Liotta et al. | 514/274 |
| 5,234,913 | 8/1993 | Furman, Jr. et al. | 514/49 |
| 5,248,776 | 9/1993 | Chu et al. | 544/310 |
| 5,270,315 | 12/1993 | Belleau et al. | 514/262 |
| 5,276,151 | 1/1994 | Liotta | 544/317 |
| 5,444,063 | 8/1995 | Schinazi | 514/262 |
| 5,539,116 | 7/1996 | Liotta et al. | 544/317 |

FOREIGN PATENT DOCUMENTS

| | | | |
|---|---|---|---|
| 0 206 497 | 12/1986 | European Pat. Off. | C07D 473/16 |
| 0 337 713 | 10/1989 | European Pat. Off. | |
| 0 375 329 | 6/1990 | European Pat. Off. | C07D 473/00 |
| 382526 | 8/1990 | European Pat. Off. | |
| 0 433 898 | 12/1990 | European Pat. Off. | |
| 0 494 119 | 7/1992 | European Pat. Off. | |
| 0 515 144 | 11/1992 | European Pat. Off. | A61K 31/505 |
| 0 515 156 | 11/1992 | European Pat. Off. | |
| 0 515 157 | 11/1992 | European Pat. Off. | |
| 0 526 253 | 2/1993 | European Pat. Off. | C07D 411/04 |
| WO90/12023 | 10/1990 | WIPO. | |
| WO 91/17159 | 11/1991 | WIPO | C07D 411/04 |
| WO 92/14729 | 9/1992 | WIPO. | |
| WO 92/15308 | 9/1992 | WIPO. | |
| WO 92/18517 | 10/1992 | WIPO. | |

OTHER PUBLICATIONS

Balzarini, J., et al., "Potent and Selective Anti–HTLV–III/LAV Activity of 2',3'–; . . . " *Biochemical and Biophysical Research Communications*, 140(2):735–742 (1986).

Borthwick, et al., "Synthesis and Enzymatic Resolution of Carbocylic 2'-Ara–Fluoro–Guanosine: A Potent New Anti–Herpetic Agent." *J. Chem. Soc. Chem. Commun.*, vol. 10, pp. 656–658 (1988).

Carter, et al., "Activities of (–)-Carbovir and 3'-Azido-3'-Deoxythymidine Against . . . ." *Antimicrobial Agents and Chemotherapy*, 34(6):1297–1300 (1990).

Chang, Chien–Neng, et al., "Deoxycytidine Deaminase–resistant Steroisomer . . . ." *J. Bio. Chem.*, 357(20):13938–13942 (1992).

Chu, C. K. et al., "An Efficient Total Synthesis of 3'-Azido-3'-Deoxythiymidine (AZT) and 3'-Azido-2',3'-Dideoxyuridine (AZDDU, CS-87) . . . ." *Tetrahedron Lett.* 5349 (1988).

Chu, et al., "Comparative Activity of 2',3'-Saturated and Unsaturated Pyrimidine and Purine Nucleosides . . . ." *Biochem. Pharm.* 37(19):3543–3548 (1988).

Chu, et al., "Structure–Activity Relationships of Pyrimidine Nucleosides as Antiviral Agents . . . ." *J. Med. Chem.* 32:612 (1989) No. 3.

Cretton, E., et al., "Catabolism of 3'-Azido-3'-Deoxythymidine in Heptaocytes and Liver Microsomes . . . ." *Molecuilar Pharmacology*, 39:258–266 (1991).

Cretton, E., et al., "Pharmokinetics of 3'-Azido-3'Dexoythymidine . . . ." *Antimicrobial Agents and Chemotherapy*, 35(5):801–807 (1991).

(List continued on next page.)

*Primary Examiner*—Mukund J. Shah
*Assistant Examiner*—Sabiha N. Qazi
*Attorney, Agent, or Firm*—Sherry M. Knowles; Jacqueline Haley; King & Spalding

[57] ABSTRACT

A method and composition for the treatment of humans infected with HIV that includes the administration of an HIV treatment amount of an enantiomerically pure β-D-dioxolanyl purine nucleoside of the formula:

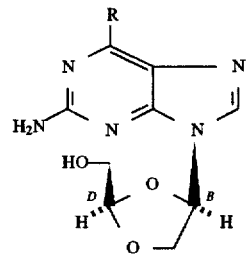

wherein R is OH, Cl, NH$_2$, or H, or a pharmaceutically acceptable salt or derivative of the compound, optionally in a pharmaceutically acceptable carrier or diluent.

13 Claims, 3 Drawing Sheets

OTHER PUBLICATIONS

Furman, et al., "The Anti–Hepatitis B Virus Activities, Cytotoxicities, and Anabolic Profiles . . . ," *Antim. Agents and Chemo.*, 36(12):2686–2692 (1992).

Gerlt, John A., *Chemical Abstracts*, 107:149790 (1987).

Gosselin, G., "Enantiomeric 2',3'–Deoxycytidine Derivatives are Potent Human Immunodeficiency Virus Inhibitors in Cell Cultures," *C.R. Acad. Sci. Paris Sci. Vie.* 317:85–89 (1994).

Hoong et al., "Enzyme–Mediated Enantioselective Preparation of Pure Enantiomers of the Antiviral Agent 2'3'–Dideoxy–5–Fluoro–3'Thiacytidine (FTC) and Related Compounds," *Journal of Organic Chem.*, 57:5563–5565 (1992).

Jeong, L., et al., "Asymmetric Synthesis and Biological Evaluation of β–L–(2R,5S)–and a–L–(2R–5R)–1,3–Oxathiolane–Pyrimidine and –Purine Nucleosides and Potential Anti–HIV Agents," *J. Med. Chem.*, vol. 36 (1993) p. 181–195.

Kim, Hea O., et al., "Asymmetric Synthesis of 1,3–Dioxolane–Pyrimidine Nucleosides and Their Anti–HIV Activity," *J. Med. Chem.*, 35:1987–1995 (1992).

Kim, H.O., et al., "L–β–(2S,4S)–and L–α–(2S,4R)–Dioxolanyl Nucleosides as Potential Anti–HIV Agents: . . . ," *J. Med. Chem.*, 1993, 36, 519–528.

Kim, H.O., et al., "1,3–Dioxolanylpurine Nucelosides (2R, 4R) and (2R,4S) with Selective Anti–HIV–1 Activity . . . ," *J.Med.Chem.* 1993, 36, 30–37.

Krenitsky, T.A., et al., "3'–Amino–2',3'–Dideoxyribonucleosides of Some Pyrimidines: Synthesis and Biological Activities," *J. Med. Chem.*, 26 (1983) pp. 891–895.

Lee, Bonita, et al., "In Vitro and In Vivo Comparison of the Abilities of Purine and . . . ," *Antimicrobial Agents and Chemotherapy*, 33(3):336–339 (1989).

Lin, et al., "Potent and Selective In Vitro Activity of 3'–Deoxythmindine–2–Ene–. . . ," *Biochem. Pharm.*, 36(17):2716 (1987).

Mahmoudian, et al., "Enzymatic Production of Optically Pure (2'R–cis)–2;–Deoxy–3'–Tiacytidine (3TC, Lamivudine): A Potent Anti–HIV Agent," *Enzyme Microb. Technol.*, 15:749–755, Glaxo Group Research Ltd., publisher (1993).

Mitsuya, H., et al., "3'–Azido–3'–Deoxythymidine (BW A 509U): An Antiviral Agent that Inhibits . . . ," *Proc. Natl. Acad. Sci., USA*, 82:7097–7100 (1985).

Mitsuya, H., et al., "Rapid In Vitro Systems for Assessing . . . ," *AIDS: Modern Concepts and Therapeutic Challenges*, S. Broder, Ed. p. 303, Marcel–Dekker, New York (1987).

Norbeck, D., et al., "A New 2',3'–Dideoxynucleoside Prototype with In Vitro Activity Against HIV," *Tetrahedron Lett.*, pp. 6263–6266 (1989).

Norin, *Chemical Abstract*, 108:146380 (1987).

Okabe, M., et al., "Synthesis of the Dideoxynucleosides ddC and CNT . . . ," *J. Org. Chem.*, 53(20):4780–4786 (1988).

Ohno, Masaji, *Chemical Abstracts*, 104:149–258 (1989).

Pirkle, et al., Advances in Chromatography, Giddings, J.C., et al., eds., vol. 27, Chap 3, pp. 73–127, Marcel Dekler, New York (1987).

Richman, D. D., et al., "The Toxicity of Azidothymidine (AZT) in the Treatment of Patients with AIDS . . . ," *N. Eng. J. Med.*, 317:192 (1987).

Saari, Walfred S., et al., "Synthesis and Evaluation of 2–Pyridinone Derivatives as HIV–1–Specific Reverse Transcriptase Inhibitors. 2. Analogues of 3–Aminopyridin–2(1H)–one," *J. Med. Chem.*, 35:3792–3802 (1992).

Satsumabayashi, S. et al., "The Synthesis of 1,3–Oxathiolane–5–one Derivatives," *Bull. Chem. Soc. Japan*, 45:913 (1972).

Schinazi, R.F., et al., "Activities of the Four Optical Isomers of 2',3'–Dideoxy–3–Thiacytidine . . . ," *Antimic. Agents & Chemo.* 36(3):672–676 (1992).

Schinazi, R.F., et al., "Insights into HIV Chemotherapy," *AIDS Research and Human Retroviruses* 8(6):963–990 (1992).

Schinazi, R.F., et al., "Pharmacokinetics and Metabolism of Racemic 2',3'–Dideoxy–5–Fluoro–3'–Thiacytidine in Rhesus Monkeys," *Antimicrobial Agents and Chemotherapy* 36(11):2432–2438 (1992).

Schinazi, R.F., et al., "Selective Inhibition of Human Immunodeficiency Viruses . . . ," *Antim. Agents and Chemo.* 36(11):2423–2431 (1992).

Schinazi, R.F., et al., "Gubstrate Specificity of *Escherichia Coli* Thymidine Phosphorylase for Pyrimidine . . . ," *Bioch. Pharm.* 44(2):199–204 (1992).

Secrist, et al., "Resolution of Racemic Carbocyclic Analogues of Purine Nucleosides Through the Action of Adenosine Deaminase. Antiviral Activity of the Carbocyclic 2'–Deoxyguanosine Enantiomers," *J. Med. Chem.*, 30:746–749 (1987).

Storer, R., et al., "The Resolution and Absolute Sterochemistry of the Enantiomeris of cis–1–2–(Hydromethyl)–1, 3–Oxathiolan–5–yl)cytosine . . . ," *Nucleosides & Nucleotides*, 12(2):225–236 (1993).

Vorbrüggen, et al, "Nucleoside Synthesis with Trimethysilyl Triflate and Perchlorate as Catalysts," *Chem. Ber.*, 114:1234–1255 (1981).

Wilson, L.J., et al., "The Synthesis and Anti–HIV Activity of Pyrimidine Dioxolanyl Nucleosides," *Bioorganic & Medicinal Chemistry Letters*, 3(2):169–174 (1993).

Wilson, L.J., et al., "A General Method for Controlling Glycosylation Stereochemistry in the Synthesis . . . ," *Tetrahedron Lett.*, 31(13):1815–1818 (1990).

Zhu, Zhou, et al., "Cellular Metabolism of 3'–Azido–2', 3'–Dideoxyuridine with Formation of 5'–O–Diphoposhexase . . . " *Molecular Pharmacology*, 38:929–938 (1990).

(±)-BCH-189     (±)-Dioxolane-T

R = t-BuPh₂Si-

1 Reagents: (a) TMSOTf, CH₂Cl₂; (b) NH₃, DME; (c) HSCH₂CH₂OH, NaOMe; (d) NH₃, EtOH; (e) n-Bu₄NF, THF

ENANTIOMERICALLY PURE β-D-DIOXOLANE NUCLEOSIDES

This application is a divisional application of U.S. Ser. No. 07/935,515 filed on Aug. 25, 1992, which is a continuation-in-part of U.S. Ser. No. 07/622,762 filed on Dec. 5, 1990, now U.S. Pat. No. 5,179,104.

The government has rights in this invention by virtue of grants from the Public Health Service of the National Institute of Allergy and Infectious Diseases, and the Department of Veterans Affairs that partially funded research leading to this invention.

BACKGROUND OF THE INVENTION

This invention is in the area of organic compounds with antiviral activity, and in particular provides a process for the preparation of enantiomerically pure β-D-dioxolane nucleosides, and methods for the treatment of viral diseases that includes administering an effective amount of one or more of the described compounds.

A number of 2',3'-dideoxynucleosides have been found to be potent antiviral agents against human immunodeficiency virus (HIV), the causative agent of acquired immunodeficiency syndrome (AIDS). AZT (3'-azido-2'-deoxythymidine, Mitsuya, H.; Broder, S. *Proc. Natl. Acad. Sci. U.S.A.*, 1986 83, 1911) was the first compound approved by the U.S. Food and Drug Administration for the treatment of patients with AIDS or AIDS-related complex. Other synthetic nucleosides have now either been approved or are undergoing various stages of clinical trials, including 2',3'-dideoxyinosine (DDI), 2',3'-dideoxycytidine (DDC) (see Yarchoan, R. et. al., Science, 1989, 245, 412), and 2'-fluoro-arabinofuranosyl-2'-3'-dideoxycytidine (Martin, T. A., et al., *J. Med. Chem.*, 1990, 33, 2137; Watanabe, K. A., et al., *J. Med. Chem.*, 1990, 33, 2145; Sterzycki, R. Z., et al., *J. Med. Chem.*, 1990 33, 2150).

After cellular phosphorylation to the 5'-triphosphate by cellular kinases, these synthetic nucleosides may be incorporated into a growing strand of viral DNA, causing chain termination due to the absence of the 3'-hydroxyl group.

The stereochemistry of nucleoside derivatives play an important role in their biological activity. The C1' position of the ribose in the nucleoside (the carbon bound to the nitrogen of the heterocyclic base) is a chiral center because the carbon is attached to four different moieties. Likewise, there is an optically active center at C4' of the nucleoside (the ring carbon bound to the hydroxymethyl group that is phosphorylated in nucleotides). In the naturally occurring nucleosides, both the base attached to the C1' and the hydroxymethyl group attached to the C4' atom are in the β-configuration (above the plane of the sugar). The corresponding non-naturally occurring α-isomers (in which the moieties are below the plane of the sugar) are rarely biologically active, and are typically toxic.

An analysis of the solid-state conformations of six active and two inactive anti-HIV nucleoside agents was recently performed to attempt to correlate the presence or absence of certain stereochemical features with high HIV activity. Van Roey, P., et al., *J. Am. Chem. Soc.*, 1988, 110, 2277; and Van Roey, P., et al., *Proc. Natl. Acad. Sci. U.S.A.*, 1989, 86, 3929.

There has been recent interest in the synthesis of nucleoside derivatives in which the 3'-carbon of the nucleoside has been replaced with a heteroatom. Norbeck, D. W., et al., in Tet. Lett., 1989, 30, 6263, reported the synthesis of (±)-1-[(2β,4β)-2-(hydroxymethyl)-4-dioxolanyl]thymine (referred to below as (±)-dioxolane-T, see FIG. 1), that results in a racemic mixture of diastereomers about the C4' atom. The product is a derivative of 3'-deoxythymidine in which the C3' atom has been replaced with an O3' atom. The product was synthesized in five steps from benzyloxyaldehyde dimethylacetal and (±)-methyl glycerate to produce a 79% yield of the 1:1 diastereomeric mixture. The X-ray crystallographic analysis of the product revealed that the dioxolane ring adopts the $^3T_4$ conformation commonly observed in ribonucleosides, with the O3' atom in the endo position. Norbeck reported that the racemic mixture of dioxolane-T exhibits an anti-HIV activity of 20 μM in ATH8 cells, and attributed the low efficacy against the virus to an effect of the endo conformation of the O3' atom. Tetrahedron Letters 30 (46), 6246, (1989).

European Patent Application Publication No. 0 337 713 and U.S. Pat. No. 5,041,449, assigned to IAF BioChem International, Inc., disclose that a generic formula of 2-substituted-4-substituted-1,3-dioxolanes exhibit antiviral activity.

Belleau, et al., in the Fifth International Conf. on AIDS, Montreal, Canada Jun. 4–9, 1990, paper No. T.C.O.1., reported a method of synthesis of cytidine nucleosides that contain oxygen or sulfur in the 3'-position. The dioxolane ring was prepared by the condensation of $RCO_2CH_2CHO$ with glycerin. As with the Norbeck synthesis, the Belleau synthesis results in a racemic mixture of diastereoisomers about the C4' carbon of the nucleoside. Belleau reported that the sulfur analog, referred to as NGBP-21 or (±) BCH-189 (see FIG. 1), has anti-HIV activity.

European Patent Application No. 92300056.6 to Belleau discloses the use of BCH-189 for the treatment of hepatitis B virus (HBV). BCH-189 is now in clinical trials under the supervision of the U.S. Food and Drug Administration.

U.S. Pat. No. 5,047,407 and European Patent Application Publication No. O 382 526, also assigned to IAF Biochem International, Inc. disclose that a generic formula of 2-substituted-5-substituted-1,3-oxathiolane nucleosides have antiviral activity.

As of the priority date of this application, a method of synthesis of a nucleoside analog with an oxygen in the 3'-position that results in an enantiomerically pure dioxolane nucleoside that has the same stereochemistry as the nucleosides found in nature (the β stereoisomer) has not been reported. There is a need for such a synthesis as a research tool to provide more information on the effect of stereochemistry on the anti-viral activity of nucleoside derivatives, and to provide new anti-HIV agents.

It is therefore an object of the present invention to provide a method of synthesis of enantiomerically pure dioxolane nucleosides.

It is another object of the present invention to provide enantiomerically pure dioxolane nucleosides with significant anti-HIV activity.

SUMMARY OF THE INVENTION

A method for the treatment of humans infected with HIV that includes administering an HIV treatment amount of an enantiomerically pure β-D-dioxolanyl purine nucleoside of the formula:

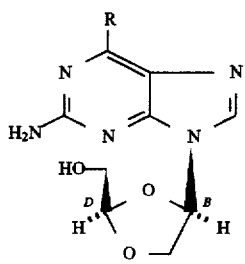

wherein R is OH, Cl, NH$_2$, or H, or a pharmaceutically acceptable salt or derivative of the compound, optionally in a pharmaceutically acceptable carrier or diluent. The compound wherein R is chloro is specifically referred to as (−)-(2R,4R)-2-amino-6-choloro-9-[(2-hydroxymethyl)-1,3-dioxolan-4-yl]purine. The compound wherein R is hydroxy is (−)-(2R,4R)-9-[(2-hydroxymethyl)-1,3-dioxolan-4-yl] guanine. The compound wherein R is amino is (−)-(2R,4R)-2-amino-9-[(2-hydroxymethyl)-1,3-dioxolan-4-yl]adenine. The compound wherein R is hydrogen is (−)-(2R,4R)-2-amino-9-[(2-hydroxymethyl)-1,3-dioxolan-4-yl]purine.

The specifically disclosed β-D-dioxolane nucleosides, or their pharmaceutically acceptable derivatives or salts or pharmaceutically acceptable formulations containing these compounds are useful in the treatment of HIV infections and other related conditions such as AIDS-related complex (ARC), persistent generalized lymphadenopathy (PGL), AIDS-related neurological conditions, anti-HIV antibody positive and HIV-positive conditions, Kaposi's sarcoma, thrombocytopenia purpurea and opportunistic infections. In addition, these compounds or formulations can be used prophylactically to retard the progression of clinical illness in individuals who are anti-HIV antibody or HIV-antigen positive or who have been exposed to HIV.

In another embodiment, the invention includes a method for the treatment of humans infected with HIV that includes administering an HIV treatment amount of a prodrug of the specifically disclosed enantiomerically pure β-D-dioxolanyl purine nucleosides. A prodrug, as used herein, refers to a pharmaceutically acceptable derivative of the specifically disclosed nucleoside, that is converted into the nucleoside on administration in vivo. Nonlimiting examples are pharmaceutically acceptable salts (alternatively referred to as "physiologically acceptable salts"), and the 5' and N$^6$ acylated or alkylated derivatives of the active compound (alternatively referred to as "physiologically or pharmaceutically acceptable derivatives"). In one embodiment, the acyl group is a carboxylic acid ester in which the non-carbonyl moiety of the ester group is selected from straight, branched, or cyclic C$_1$-C$_{20}$ alkyl alkoxyalkyl including methoxymethyl; aralkyl including benzyl; aryloxyalkyl such as phenoxymethyl; aryl including phenyl optionally substituted with halogen, C$_1$ to C$_4$ alkyl or C$_1$ to C$_4$ alkoxy; a dicarboxylic acid such as succinic acid; sulfonate esters such as alkyl or aralkyl sulphonyl including methanesulfonyl; and the mono, di and triphosphate esters. As used herein, the term alkyl specifically includes but is not limited to methyl, ethyl, propyl, butyl, pentyl, hexyl, isopropyl, isobutyl, sec-butyl, t-butyl, isopentyl, amyl, t-pentyl, cyclopentyl, and cyclohexyl. As used herein, the term acyl specifically includes but is not limited to acetyl, propionyl, butyryl, pentanoyl, 3-methylbutyryl, hydrogen succinate, 3-chlorobenzoate, benzoyl, acetyl, pivaloyl, mesylate, propionyl, valeryl, caproic, caprylic, capric, lauric, myristic, palmitic, stearic, and oleic. Modifications of the active compound, specifically at the N$^6$ and 5'-O positions, can affect the bioavailability and rate of metabolism of the active species, thus providing control over the delivery of the active species.

The enantiomerically pure β-D-dioxolanyl purine nucleoside can be converted into a pharmaceutically acceptable ester by reaction with an appropriate esterifying agent, for example, an acid halide or anhydride. The nucleoside or its pharmaceutically acceptable derivative can be converted into a pharmaceutically acceptable salt thereof in a conventional manner, for example, by treatment with an appropriate base. The ester or salt can be converted into the parent nucleoside, for example, by hydrolysis.

The invention as disclosed also includes an asymmetric process for the preparation of enantiomerically pure β-D-dioxolane-nucleosides. The process involves the initial preparation of (2R,4R)- and (2R,4S)-4-acetoxy-2-(protected-oxymethyl)-dioxolane from 1,6-anhydromannose, a sugar that contains all of the necessary stereochemistry for the enantiomerically pure final product, including the correct diastereomeric configuration about the 1 position of the sugar (that becomes the 4'-position in the later formed nucleoside).

The (2R,4R)- and (2R,4S)-4-acetoxy-2-(protected-oxymethyl)dioxolane is condensed with a desired heterocyclic base in the presence of SnCl$_4$, other Lewis acid, or trimethylsilyl triflate in an organic solvent such as dichloroethane, acetonitrile, or methylene chloride, to provide the stereochemically pure dioxolane-nucleoside.

Any desired enantiomerically pure β-D-dioxolane purine or pyrimidine nucleoside can be prepared according to the process disclosed herein. The product can be used as a research tool to study the inhibition of HIV in vitro or can be administered in a pharmaceutical composition to inhibit the growth of HIV in vivo.

DETAILED DESCRIPTION OF THE INVENTION

As used herein, the term "enantiomerically pure" refers to a nucleoside composition that includes at least 97% of a single enantiomer of that nucleoside.

I. Preparation of Enantiomerically Pure Dioxolane Nucleosides

In preparing enantiomerically pure dioxolane nucleosides, care should be taken to avoid strong acidic conditions that would cleave the dioxolane ring. Reactions should be performed, if possible, in basic or neutral conditions, and when acidic conditions are necessary, the time of reaction should be minimized.

A. Preparation of Enantiomerically Pure β-D-Dioxolane-Nucleosides

Figure 1:
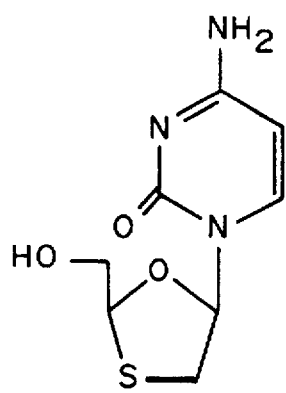
FIG. 1 is an illustration of the chemical structures of (±)-1-[(2β,4β)-2-(hydroxymethyl)-4-dioxolanyl]thymine (dioxolane-T) and (±)-1-[(2β,4β)-2-(hydroxymethyl)-4-(1,3-thioxolane)]thymine (BCH-189).
Figure 1:
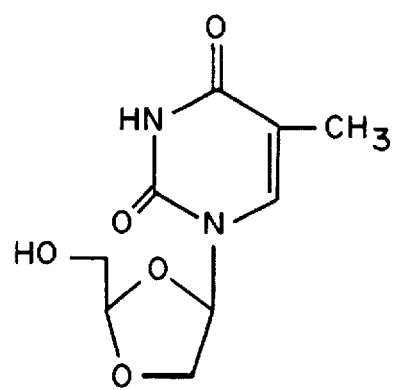
Figure 2:
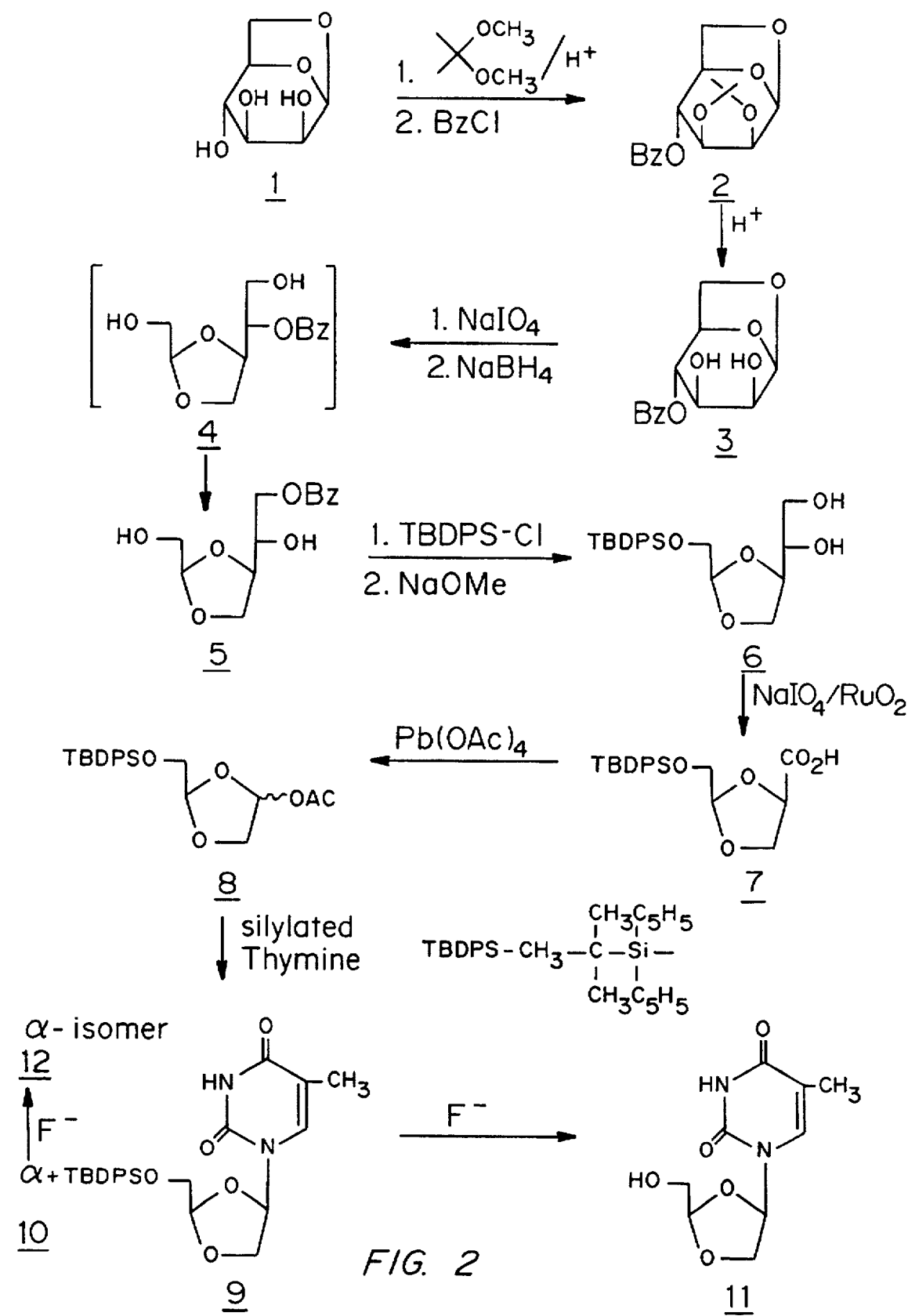
FIG. 2 is an illustration of the method of synthesis of enantiomerically pure β-D-(−)-dioxolane-thymine.

The key starting material for the synthesis of enantiomerically pure β-D-dioxolane-nucleosides is 1,6-anhydromannose (compound 1, FIG. 2). This sugar contains all of the necessary stereochemistry for the enantiomerically pure final product (see for example, compound 11, FIG. 2).

including the correct diastereomeric configuration about the 1 position of the sugar (that becomes the 4'-position in the later formed nucleoside). 1,6-Anhydromannose can be prepared according to procedures described in Knauf, A. E.; Hann, R. M.; Hudson, C. S. J. Am. Chem. Soc., 1941, 63, 1447; and Zottola, M. A.; Alonso, R.; Vite, G. D.; Fraser-Reid, B. J. Org. Chem., 1989, 54, 6123. Prior syntheses of dioxolane nucleosides have used racemic mixtures of starting materials for the preparation of the ribose moiety. When the syntheses begin with a racemic mixture of reagents, undesirable racemic mixtures of enantiomeric nucleoside products have been produced. The mixtures are very difficult to separate and significantly increase the cost of the final product. Further, the inclusion of nonnaturally occurring isomers increases the toxicity of the product.

The 1,6-anhydromannose is converted to its isopropylidene derivative with dimethoxypropane and p-toluenesulfonic acid, which, without isolation, is benzoylated in the 4-position to compound 2 (see FIG. 2). An acyl group can also be used to protect the 4-position. The isopropylidene group of compound 2 is then removed by a catalytic amount of an acid such as sulfuric acid, hydrochloric acid, formic acid, trifluoroacetic acid, sulfamic acid, in 60% aqueous dioxane or other suitable organic solvent at a temperature range of approximately 0° to 50° C. to give (−)-1,6-anhydro-4-0-benzoyl-β-D-mannopyranose in high yield as a white solid.

In the next step, the glycol of (−)-1,6-anhydro-4-0-benzoyl-D-mannopyranose is oxidatively cleaved by treatment with NaIO$_4$ in H$_2$O/EtOH (1:1) for one hour at approximately room temperature to produce to the corresponding dialdehyde. Lead tetraacetate can also be used as the oxidizing reagent for this reaction. The dialdehyde is immediately reduced in situ with any suitable reducing agent, including NaBH$_4$, diisobutylaluminum hydride (DIBAL-H), lithium borohydride (LiBH$_4$), or sodium bis(2-methoxyethoxy)-aluminum hydride (Red-Al), at approximately room temperature or below. Under the conditions of reaction, compound 4 isomerizes by benzoyl migration from a secondary to a primary position to produce (−)-(2R,4R)-4-(2-benzoxy-1-hydroxyethyl)-2(hydroxymethyl)-dioxolane (compound 5, FIG. 2).

The 2-position of the dioxolane is then protected with a suitable oxygen protecting group, for example, a trisubstituted silyl group such as trimethylsilyl, dimethylhexylsilyl, t-butyldimethylsilyl, t-butyldiphenylsilyl, trityl, alkyl group, acyl groups such as acetyl, propionyl, benzoyl, p-NO$_2$ benzoyl, or toluyl, methylsulfonyl, or p-toluylsulfonyl. A preferred protecting group is t-butyldiphenylsilyl. After protecting the 2-position of the dioxolane, the benzoyl group is removed from the 2-hydroxyethyl-position with a strong base such as sodium methoxide or ammonia in methanol at approximately 0 to 50° C. to produce (−)-(2R,4R)-2-(protected-O-methyl)-4-(1,2-dihydroxyethyl)-dioxolane (compound 6, FIG. 2) in high yield.

In the next step, the 1,2-dihydroxyethyl group in the 4-position of the dioxolane is converted to a carboxylic acid with an oxidizing agent such as NaIO$_4$/RuO$_2$, or lead tetraacetate, at approximately 0° to 50° C. to produce (+)-(2R,4R)-2-(protected-oxymethyl)-4-carboxyldioxolane (see compound 7, FIG. 2).

A modified Hunsdiecker reaction (Dhavale, D.; et al., Tetrahedron Lett., 1988, 29, 6163) is then carried out in ethyl acetate with Pb(OAc)$_4$ to convert (+)-(2R,4R)-2-(protected-oxymethyl)-4-carboxyldioxolane to the corresponding key intermediates (2R,4R)- and (2R,4S)-4-acetoxy-2-(protected-oxymethyl) dioxolane (see compound 8, FIG. 2) in good yield.

B. Condensation of a Heterocyclic Base with the Dioxolane Derivative

In the next step of this reaction scheme, the enantiomerically pure dioxolane prepared as described in Section A. is condensed with a protected base in the presence of trimethylsilyl triflate (trimethylsilyl trifluoromethanesulfonate) or a Lewis acid in a dry organic solvent.

Any aromatic compound, and in particular a purine or pyrimidine, containing a nitrogen that is capable of reaction with a center of electron deficiency can be used in the condensation reaction. Purine bases include but are not limited to adenine, hypoxanthine, 2,6-diaminopurine, 6-amino-2-chloropurine, 2-aminopurine, N$^6$-alkylpurines, N$^6$-benzylpurine, N$^6$-halopurine, and guanine. Pyrimidine bases include but are not limited to thymine, cytosine, 6-azapyrimidine, 2-mercaptopyrimidine, and uracil. Functional oxygen and nitrogen groups on the heterocyclic base should be protected before condensation with the sugar if undesired side reactions occur during the synthetic procedure. Protecting groups are well known to those skilled in the art, and include trimethylsilyl, dimethylhexylsilyl, t-butyldimethylsilyl, and t-butyldiphenylsilyl, tritylmethyl, alkyl groups, acyl groups such as acetyl and propionyl, methylsulfonyl, and p-toluylsulfonyl.

Friedel-Crafts catalysts (Lewis acids) that can be used in the condensation reaction include SnCl$_4$, ZnCl$_4$, TiCl$_4$, AlCl$_3$, FeCl$_3$, BF$_3$-diethylether, and BCl$_3$. These catalysts require anhydrous conditions because the presence of water reduces their activity. The catalysts are also inactivated in the presence of organic solvents with active hydrogens, such as alcohols and organic acids. The catalysts are typically used in solvents such as carbon disulfide, methylene chloride, nitromethane, 1,2-dichloroethane, nitrobenzene, tetrachloroethane, chlorobenzene, benzene, toluene, dimethylformamide, tetrahydrofuran, dioxane, or acetonitrile. Anhydrous aluminum chloride is not soluble in carbon disulfide. Niedballa, et al., J. Org. Chem. 39, 25 (1974). The preferred catalyst is SnCl$_4$. The preferred solvent is 1,2-dichloroethane. Trimethylsilyl triflate can be used under the same conditions described above for the Friedel-Crafts catalysts. The reaction proceeds at a temperature range of from −10° C. to 200° C. The choice of catalyst for condensation will affect the final product ratio of α to β nucleoside product. For example, condensation of the intermediates (2R,4R)- and (2R,4S)-4-acetoxy-2-(t-butyldiphenylsilyoxymethyl) dioxolane (compound 8, FIG. 2) with silylated thymidine in the presence of trimethylsilyl triflate in CH$_2$Cl$_2$ gave a mixture of (−)-1-[(2R,4R)-2-(t-butyldiphenylsilyloxymethyl)-4-dioxolanyl]thymine 9-(45%) and (+)-1-[(2R,4S)-2-(t-butyldiphenylsilyloxymethyl)-4-dioxolanyl] thymine 10-α (29%). However, the reaction with SnCl$_4$, produced exclusively β-isomer 9 with trace amounts of α-isomer 10 detectable on TLC.

Figure 3:
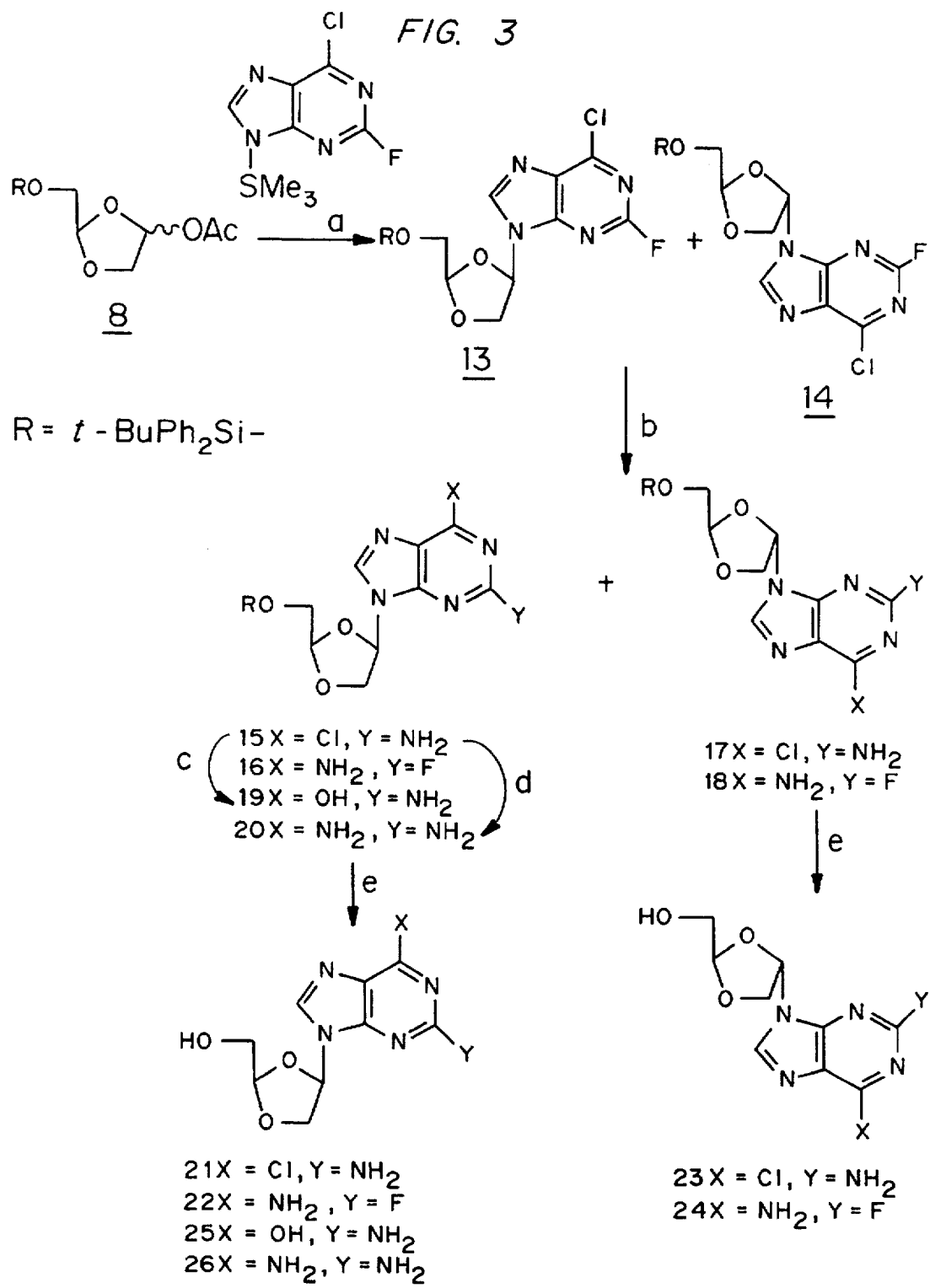
FIG. 3 is an illustration of the method of preparation of a variety of enantiomerically pure β-D-(−)-dioxolanyl purine nucleosides.

2,6-Disubstituted purine derivatives were synthesized by the condensation of acetate 8 with the silylated 6-chloro-2-fluoropurine, which gave a mixture (α/β=1/1.3) of 14 and 13 (FIG. 3). The initially formed N$^7$-isomer was again converted to the N$^9$-isomer during stirring overnight at room temperature. The analytical sample was obtained from the separation of α,β-mixture to the individual isomers 13 and 14 by a preparative TLC using CH$_2$CL$_2$-acetone (19:1) as the developing solvents. However, for the purpose of preparing the final products 21–24, the mixture of 13 and 14 was treated with NH$_3$ in DME (Robins, M. J.; Vznanski, B. Nucleic acid related compounds. 34. Non-aqueous Diazotization with tert-Butyl nitrite. Introduction of Fluorine, Chlorine, and Bromine at C-2 of Purine Nucleosides. Can. J. Chem. 1981, 2608) to give a mixture of 21–24, which was separated to the individual isomers 15 (24%), 16 (18.6%), 17 (25.8%) and 18 (16%). The guanine 19 and 2,6-diamino 20 derivatives were prepared by the treatment of 15 with 2-mercaptoethanol/NaOMe and ammonia in ethanol, respectively. The free nucleosides 21–26 were obtained upon treatment of the corresponding 5'-silylated nucleosides with n-Bu$_4$NF in good yields. The α-isomers 23 and 24 were also prepared by the similar procedure as the β-isomers.

In the final step of this method of preparation of enantiomerically pure (–)-β-D-dioxolane-nucleosides, the 5'-O-position of the nucleoside is deprotected. Desilylation can be carried out with a variety of reagents, including acetic acid, trifluoroacetic acid, hydrogen fluoride, n-tetrabutylammonium fluoride, potassium fluoride and pyridinium HCl. For example, desilylation of compounds 9 and 10 with tetrabutylammonium fluoride gave the desired free nucleosides 11 and 12, respectively (FIG. 2). Acetic acid is preferred for commercial scale use because it is inexpensive. Other reagents for desilylation are known to those skilled in the art. Deacylation is accomplished in acid or base. 5-O-Ethers can be cleaved with BCl$_3$ or trimethylsilyl iodide.

The method of preparation of enantiomerically pure β-D-dioxolane-nucleosides is further illustrated in the following working examples. Example 1 sets out in detail a method for the preparation of (2R,4R)- and (2R,4S)-4-acetoxy-2-(t-butyldiphenylsilyoxymethyl) dioxolane (compound 8, FIG. 2). Example 2 sets out the preparation of (–)-1-[(2β,4β)-2-(hydroxymethyl)-4-dioxolanyl]thymine, referred to as (–)-β-D-dioxolane-T. The enumeration of compounds in Example 2 refer to structures set out in FIG. 2. Example 3 provides detailed examples for the preparation of a number of enantiomerically pure β-D-dioxolanyl nucleosides, including (–)-(2R,4R)-2-amino-6-chloro-9-[(2-hydroxymethyl)-1,3-dioxolan-4-yl]purine, (–)-(2R,4R)-9-[(2-hydroxymethyl)-1,3-dioxolan-4-yl]guanine, and (–)-(2R,4R)-2-amino-9-[(2-hydroxymethyl)-1,3-dioxolan-4-yl]adenine.

EXAMPLE 1

Preparation of (2R,4R)- and (2R,4S)-4-Acetoxy-2-(tbutyldiphenylsilyloxymethyl)dioxolane (Compound 8).

(–)-1,6-Anhydro-2,3-isopropylidene-4-0-benzoyl-β-D-mannopyranose 1,6-anhydro-β-D-mannopyranose (compound 1) was mixed with acetone (800 ml) and methanol (300 ml) and stirred for approximately thirty minutes until only a free-flowing solid remained. Dimethoxypropane (300 ml), and p-toluenesulfonic acid (5 g) were then added, and the mixture stirred for 2 hours.

The reaction mixture was then made basic with triethylamine (pH 8), and filtered to remove the white solid material. The solvents were evaporated, and the residue taken up in ethyl acetate and then crystallized to obtain 4 grams of the 2,3-isopropylidenated product as clear needles.

To a solution of the 1,6-anhydro-2,3-isopropylidene-β-D-mannopyranose (5.01 g, 0.025 mol) in pyridine (40 ml) was added dropwise benzoyl chloride (3.74 ml, 0.062 mol) at 0° C. The mixture was stirred for 45 minutes at 0° C. Ice was then added to the reaction mixture to remove excess benzoyl chloride. The solvent was evaporated under vacuum and the residue was dissolved in ethyl acetate (200 ml). The organic layer was washed with water, sat. NaHCO$_3$ and brine. The resulting material was dried over anhydrous MgSO$_4$, filtered, and then evaporated to give (–) 1,6-anhydro-2,3-isopropylidene-4-0-benzoyl-β-D-mannopyranose crude product (compound 2, 8.7 g) as yellowish solid.

(–)-1,6-Anhydro-4-0-benzoyl-β-D-mannopyranose (3).

To a solution of 1,6-anhydro-4-0-benzoyl-2,3-isopropylidene-β-D-mannopyranose 2 (10.0 g, 32.6 mmole) in 60% aqueous dioxane (820 ml) was added concentrated H$_2$SO$_4$ (3.36 ml). The mixture was stirred at 70°–80° C. for 15 hours, and then cooled in an ice bath, neutralized with NaHCO$_3$ and concentrated until half of the original volume remained. The solution was then extracted with ethyl acetate and the combined organic layers washed with saturated NaHCO$_3$ solution and water, dried, and evaporated to give 3 as a white solid. The solid was crystallized from CH$_2$Cl$_2$-n-hexane to yield 3 (7.4 g, 85.3%) as white solid: [α]$^{25}$D-154.7° (C, 0.21 MeOH); $^1$H NMR (DMSO-d$_6$): δ 3.56–4.61 (m, 5H, 2,3,5,6-H), 4.82 (d, J=8.1 Hz, 1H, OH D$_2$O exchangeable), 5.02 (s, 1H, 4-H), 5.09 (d, J=3.7 Hz, 1H, OH, D$_2$O exchangeable), 5.28 (s, 1H, 1-H), 7.46–8.05 (m, 5H, Ar-H); IR (KBr) 3410, 1710 cm$^{-1}$; Anal. Calcd for C$_{13}$H$_{14}$O$_6$: C, 58.64; H, 5.31. Found: C, 58.51; H, 5.34.

(–)-(2R,4R)-4-(2-Benzoxy-1-hydroxyethyl)-2-(hydroxymethyl)dioxolane (5).

To a solution of 3 (7.4 g, 27.8 mmole) in 95% ethanol (200 ml) was added a solution of NaIO$_4$ (6.54 g, 30.7 mmole) in water (200 ml). The mixture was stirred at room temperature for 1 hour. After checking to insure the complete conversion of diol to dialdehyde by thin layer chromatography, the reaction mixture was concentrated to the half of the original volume. Methanol (200 ml) was added to the residue and the mixture was cooled to 50° C. Sodium borohydride (4.2 g, 111.0 mmole) was added to the mixture portion-wise for 5 minutes and the mixture was stirred at 50° C. for 10 minutes, neutralized with glacial acetic acid and concentrated to yield crude 3 as yellow oil. The oil was purified by column chromatography over silica gel to yield pure 3 as colorless oil, that was crystallized from diethyl ether/n-hexane to yield 5 (6.12 g, 82%) as white solid: [α]$^{25}$D-18.5° (C 0.20, methanol); $^1$H NMR (DMSO-d$_6$): δ 3.47 (dd, J=5.9, 3.7 Hz, 2H, CH$_2$OH), 3.72–4.14 (m, 4H, 4, 5-H and CHOH), 4.27–4.95 (m, 2H, CH$_2$OBz), 4.81–4.95 (m, 2-H and pri OH), 5.43 (d, J=5.5 Hz, 1H, sec OH, D$_2$O exchangeable), 7.43–8.09 (m, 5H, Ar—H); Anal. Calcd for C$_{13}$H$_{16}$O$_6$: C, 58.19; H, 6.02. Found: C, 58.09; H, 6.01.

(–)-(2R,4R)-4-(2-Benzoxy-1-hydroxyethyl)-2-(t-butyldiphenylsilyloxy-methyl)-dioxolane.

To a solution of 3 (2.8 g, 10.4 mmole) and imidazole (2.04 g, 30.0 mmole) in dimethylformamide (40 ml) was added t-butyldiphenylsilyl chloride (3 ml, 11.5 mmole). The mixture was stirred at room temperature for 2 hours. The reaction mixture was evaporated to yield a yellow oil, that was purified by column chromatography over silica gel to yield 4 (4.48 g, 85%) as a colorless oil; [α]$^{25}$D-14.20 (C 0.26, methanol); $^1$H NMR (DMSO-d$_6$)δ: δ1.00 (s, 9H, t-Bu), 3.68–3.87 (m, 3H, CH$_2$OTBDPS and CHOH), 3.98–4.16 (m, 3H, 4,5-H), 4.20–4.55 (m, 2H, CH$_2$OBz), 5.07 (t, J=3.3 Hz, 1H, 2-H), 5.47 (d, J-5.7 Hz, 1H, OH, D$_2$O exchangeable), 7.40–8.33 (m, 1OH, Ar—H); Anal. Calcd for C$_{29}$H$_{34}$O$_6$Si: C, 68.73; H, 6.79. Found: C, 68.86; H, 6.83.

(–)-(2R, 4R)-2-(t-Butyldiphenylsilyloxymethyl)-4-(1,2-dihydroxyethyl)-dioxolane (6).

To a solution of (–)-(2R,4R)-4-(2-benzoxy-1-hydroxyethyl)-2-(t-butyldiphenylsilyloxy-methyl)-dioxolane (2.52 g, 5.0 mmole) in methanol (40 ml) was added a 0.078M solution of sodium methoxide (7.3 ml) in methanol. The mixture stirred at room temperature for two hours. The mixture was neutralized with acetic acid and concentrated. The residue was then portioned between ethyl acetate and water, and the aqueous layer extracted with ethyl acetate. The combined organic layers were washed with a saturated $NaHCO_3$ solution and then water, and then dried, evaporated, and purified by column chromatography over silica gel to yield 6 (1.9 g, 95%) as colorless oil: $[\alpha]^{25}D$-2° (C 0.25, MeOH); $^1H$ NMR (DMSO-$d_6$) δ1.00 (s, 9H, t-Bu), 3.40–3.52 (m, 3H, $CH_2OH$ and CHOH), 3.64 (d, J=3.7 Hx, 2H, $CH_2OTBDPS$), 3.82–3.95 (m, 3H, 4.5-H), 4.49 (t, J-5.3 Hz, 1H, pri OH, $D_2O$ exchangeable), 4.82 (d, J=5.1 Hz, 1H, sec OH, $D_2O$ exchangeable), 5.01 (t, J-3.7 Hz, 1H, 2-H), 7.36–7.71 (m, 10H, Ar—H); Anal. Calcd for $C_{22}H_{33}H_{30}O_5Si$: C, 65.63; H, 7.53. Found: C, 65.72; H, 7.52.

(+)-(2R,4R)-2-(t-Butyldiphenylsilyloxymethyl)-4-carboxyldioxolane (7).

To a biphasic solution of 6 (1.6 g, 4.0 mmole) in $CH_3CN$ (8 ml), $CCl_4$ (8 ml) and $H_2O$ (12 ml) was added $NaIO_4$ (3.59 g, 16.8 mmole) and $RuO_2$ hydrate (8.5 mg). The mixture was vigorously stirred at room temperature for 5 hours. Methylene chloride (40 ml) was added to the mixture. The organic layer was separated. The aqueous layer was extracted with $CH_2Cl_2$. The combined organic layers were washed with water, filtered through celite pad and then concentrated to yield crude 7 (1.2 g, 77.4%) as black oil, that was used in the next reaction without further purification. For analytical purposes crude 7 was purified by column chromatography over silica gel to yield 7 as a white foam: $[\alpha]^{25}D$+15.7° (C 0.28, MeOH); $^1H$ NMR (DMSO-$d_6$) δ 0.99 (s, 9H, t-Bu), 3.43–4.05 (m, 4H, 5-H and $CH_2OTBDPS$), 4.25 (t, J=6.8 Hz, 1H, 4-H), 5.04 (dd, J=5.1, 3.7 Hz, 1H, 2-H), 7.38–7.72 (m, 10H, Ar—H).

(2R,4R)- and (2R,4S)-4-Acetoxy-2-(t-butyldiphenylsilyoxymethyl) dioxolane (8).

To a solution of 7 (0.46 g, 1.14 mmole) in ethyl acetate (10 ml) was added pyridine (0.09 ml, 1.25 mmole) and Pb(OAc)$_4$ (0.66 g, 1.49 mmole). The mixture was stirred at room temperature for 15 hours under $N_2$, and then filtered through celite pad, and then concentrated and purified by column chromatography over silica gel to yield 8 (0.29 g, 63.5%) as a colorless oil: $^1H$ NMR (CDCl$_3$) δ 1.06 and 1.10 (s, 9H, t-Bu), 1.92 and 2.06 (s, 1H, $CH_3$), 3.71–4.24 (m, 4H, 5-H and $CH_2OTBDPS$), 5.25 and 5.38 (t, J=4.3 and 3.3 Hz each, 1H, 2-H), 6.27–6.41 (m, 1H, 4-H), 7.20–7.72 (m, 1OH, Ar—H); IR (KBr) 3400, 1620 $cm^{-1}$.

EXAMPLE 2

Preparation of (−)-1-[(2R,4R)-2-(Hydroxymethyl)-4-dioxolanyl]thymine (11).

(−)-1-[(2R,4R)-2-(t-Butyldiphenylsilyloxymethyl)-4-dioxlanyl] thymine (9) and (+)-1-[(2R,4S)-2-(t-Butyldiphenylsilyloxymethyl)-4-dioxolanyl] thymine (10).

To a suspension of thymine (0.15 g, 1.2 mmole) in haxamethyldisilazane (10 ml) was added a catalytic amount of (NH$_4$)$_2$SO$_4$, and the mixture refluxed for 3 hours. The clear solution obtained was concentrated to yield silylated thymine as a colorless oil. A solution of 8 (0.24 g, 0.6 mmole) in $CH_2Cl_2$ (5 ml) was added to a solution of silylated thymine in $CH_2Cl_2$ (5ml) and the mixture cooled to 5° C. To the cooled mixture was added trimethylsilyl triflate (0.23 ml, 1.2 mmole), and the mixture stirred at room temperature for 1 hour under $N_2$. A saturated $NaHCO_3$ solution (20 ml) was added to the mixture, and the mixture again stirred at room temperature for 30 minutes. The organic layer was then separated and the aqueous layer extracted with $CH_2Cl_2$. The combined organic layer was washed with a saturated $NaHCO_3$ solution and water, dried, concentrated and separated by column chromatography over silical gel to yield 9 (0.125 g, 44.6%) as white foam and 10 (0.08 g, 28.6%) as white foam: 9 (-form); $[\alpha]^{25}D$-6.98° (C 0.43, MeOH); $^1H$ NMR (CDCl$_3$) δ 1.08 (s, 9H, t-Bu), 1.67 (s, 3H, CH$_3$), 3.92 (d, J=3.2 Hz, 2H, $CH_2OTBDPS$), 4.14 (d, J=4.0 Hz, 2H, 5-H), 5.06 (t, J=3.2 Hz, 1H, 2-H), 6.36 (t, J+4.0 Hz, 1H, 4-H), 7.26–7.75 (m, 10H, Ar—H), 9.51 (bnr S, 1H, H═NH); UV (MeOH)) λ$_{max}$ 265.0 (pH 2); 264.4 nm (pH 11); Anal. Calcd for $C_{25}H_{30}O_5N_2Si$: C, 64.34; H, 6.49; N, 6.00. Found C, 64.28; H, 6.51; N, 5.98:

10 (α-form); $[\alpha]^{25}D$+11.3° (C 0.23, MeOH); $^1H$ NMR (CDCl$_3$) δ 1.08 (s, 9H, t-Bu), 1.94 (d, J=1.2 Hz, 3H, CH$_3$), 3.70 (d, J=3.2 Hz, 2H, $CH_2OTBDPS$), 4.01 (dd, J=9.5, 2.3 Hz, 1H, 5H), 4.35 (dd, J=9.5, 5.3 Hz, 1H, 5-H), 5.55 (t, J=3.2 Hz, 1H, 2-H), 6.32 (dd, J=5.3, 2.3 Hz, 1H, 4-H), 7.17 (d, J=1.2 Hz, 1H, 6'-H), 7.37–7.74 (m, 10H, Ar—H), 9.57 (br s, 1H, NH); UV (MeOH)λ$_{max}$ 265.0; (pH 2); 264.5 nm (pH 11); Anal. Calcd for $C_{25}H_{30}O_5N_2Si$: C, 64.34; H, 6.49; N, 6.00. Found C, 64.23; H, 6.51; N, 5.93.

(−)-1-[(2R,4R)-2-(Hydroxymethyl)-4-dioxolanyl]thymine (11).

To a solution of 9 (93.3 mg, 0.2 mmole) in tetrahydrofuran (THF) (3 ml) was added a 1.0M solution of tetra-n-butylammonium fluoride in THF (0.24 ml, 0.24 mmole) and the mixture stirred at room temperature for 1 hour. The mixture was then concentrated and purified by column chromatography over silica gel to yield 11 (42 mg, 92.1%) as white solid: $[\alpha]^{25}D$-18.8° (C o.17, MeOH); $^1H$ NMR (DMSO-$d_6$) δ 1.75 (d, J=1.2 Hz, 3H, CH$_3$), 3.63 (dd, J+6.0, 2.6 Hz, 2H, CH$_2$OH), 4.03 (dd, J=9.9, 5.5 Hz, 1H, 5-H), 4.22 (dd, J=9.9, 2.0 Hz, 1H, 5-H), 4.90 (t, J=2.6 Hz, 1H, 2-H), 5.16 (t, J-t.0 Hz, 1H, OH), 6.21 (dd, J=5.5, 2.0 Hz, 1H, 4-H), 7.67 (d, J=1.2 Hz, 1H, 6'-H), 11.27 (br s, 1H NH); UV (H$_2$) max 266.0 (ε 10757); 266.5 (ε 9894) (pH 2); 266.3 (ε 8397) (pH 11); Anal. Calcd for $C_9H_{12}O_5N_2$: C, 47.36; H, 5.31; N, 12.28. found: c, 47.28; H, 5.34; N, 12.29.

(+)-1-[(2R,4S)-2-(Hydroxymethyl)-4-dioxolanyl]thymine (12).

Deprotection of 10 (60 mg, 0.13 mmole) according to same procedure as described above for 11 yielded 12 (26 mg, 87.6%) as a white foam: $[\alpha]^{25}D$+10.7° (C 0.15, MeOH); $^1H$ NMR (DMSO-$d_6$) δ 1.79 (s, 3H, CH$_3$), 3.43 (dd, J=6.0, 3.7 Hz, 2H, CH$_2$OH), 4.02 (dd, J=9.5, 3.3 Hz, 1H, 5-H), 4.28 (dd, J=9.5, 5.6 Hz, 1H, 5-H), 5.00 (t, J=6.0 Hz, 1H, OH), 5.47 (t, J=3.7 Hz, 1H, 2-H), 6.17 (dd, J=5.6, 3.3 Hz, 1H, 4-H), 7.43 (d, J=1.2 Hz, 1H, 6'-H), 11.32 (br s, 1H NH); UV (H$_2$O)λ$_{max}$ 266.5 (ε 9454); 266.5 (ε 9199) (pH 2); 266.3 (ε 6925) (pH=11); Anal. Calcd for $C_9H_{12}O_5N_2$: C, 47.36; H, 5.31; N, 12.28. found: C, 47.22; H.5.32; N, 12.16.

EXAMPLE 3

Preparation of Enantiomerically Pure β-D-Dioxolanyl Purine Nucleosides (2R,4R) and (2R,4S)-9-[[2-[(tert-Butyldiphenylsilyl)oxy]methyl]-1,3-dioxolan-4-yl]-6-chloro-2-fluoropurine (13 and 14).

A mixture of 2-fluoro-6-chloropurine (4.05 g, 23.47 mmol) and ammonium sulfate (catalytic amount) in hexamethyldisilazane (940 mL) was refluxed for 2 hours. The resulting solution was concentrated under anhydrous conditions to yield silylated 2-fluoro-6-chloropurine as a white solid. To a cooled (0° C.) and stirred solution of silylated 2-fluoro-6-chloropurine (5.69 g, 23.69 mmol)b and compound 8 (7.84 g, 19.57 mmol) in dry methylene chloride (175 mL) was added TMSOTf (4.41 mL, 23.44 mmol). The reaction mixture was warmed to room temperature and stirred for 16 hours, during which time, all the initially formed $N_7$ condensed product was converted to $N_9$-isomer. The reaction mixture was quenched with saturated $NaHCO_3$ solution (50 mL) and stirred for an additional 20 minutes at room temperature, evaporated to dryness under reduced pressure. The residue was dissolved in ethyl acetate (200 mL), washed with water and brine, dried (anhydrous $Na_2SO_4$), filtered and evaporated to give a solid residue, which was purified by silica gel column chromatography (20% EtOAc in hexanes) to afford a mixture of β-anomer 19 and α-anomer 20 (1.3:1; β/α) as a white crystalline solid (6.30 g, 62.8%). The analytical sample was purified by preparative TLC using $CH_2Cl_2$-acetone (19:1) as the developing system to give 13 ($R_f$=0.5p0) and 14 ($R_f$=0.55) for NMR characterization: UV (MeOH) $\mu_{max}$ 269.0 nm.

(−)-(2R,4R)-2-Amino-9-[[2-[(tert-butyldiphenylsilyl)oxy] methyl]-1,3-dioxolan-4-yl]-6-chloropurine (15), (−)-(2R, 4R)-9-[[2-[(tert-Butyldiphenylsilyl)oxy]methyl]-1,3-dioxolan-4-yl]-2-fluoroadenine (16), (+)-(2R,4S)-2-Amino-9-[[2-[(tert-butyldiphenylsilyl)oxy]methyl]-1,3-dioxolan-4-yl]-6-chloropurine (17) and (+)-(2R,4S)-9-[[2-[(tert-Butyldiphenylsilyl)oxy]methyl]-1,3-dioxolan-4-yl]-2-fluoroadenine (18).

Dry ammonia gas was bubbled into a stirred solution of 13 and 14 (6.25 g, 12.18 mmol) in DME (125 mL) overnight). The solvent was evaporated under reduced pressure and the residue was subjected to chromatographic separation of the four compounds on a silica gel column (20–30% ethyl acetate in $CH_2Cl_2$). 15 ($R_f$=0.35, 1.49 g, 24%): a white crystalline solid. UV (MeOH) $\lambda_{max}$ 309.5 nm. Anal. ($C_{25}H_{28}ClN_5O_3Si$) C, H, Cl, N. 16 ($R_f$=0.21, 1.12 g, 18.6%): colorless needles. UV (MeOH) $\lambda_{max}$261.0, 268.0 (sh) nm. Anal., ($C_{25}H_{28}FN_5O_3Si$) C, H, F, N. 17 ($R_f$=0.43, 1.60 g, 25.76%): a white crystalline solid. UV (MeOH) $\lambda_{max}$ 261.0, 269.0 (sh) nm. Anal. ($C_{25}H_{28}FN_5O_3Si$) C, H, F, N. 18 ($R_f$=0.12, 0.96 g, 16%), a microcrystalline solid. UV (methanol) $\lambda_{max}$ 261.0, 269.0 (sh) nm. Anal. ($C_{25}H_{28}FN_5O_3Si$) C, H, F, N.

(−)-(2R,4R)-2-Amino-6-chloro-9-[(2-hydroxymethyl)-1,3-dioxolan-4-yl]purine (15).

A solution of 15 (0.46 g, 0.91 mmol) in THF (20 mL) was treated with 1M n-$Bu_4NF$/THF (1.1 mL, 1.1 mmol) to give 21 ($R_f$=0.50, 0.21 g, 84%) as a crystalline solid, which was recrystallized from MeOH: UV ($H_2O$) $\lambda_{max}$ 307.0 nm (ε 8.370) (pH7), 307.5 (ε 8.590) (pH 2), 307.0 (8.800) (pH 11). Anal. ($C_9H_{10}ClN_5O_3$) C, H, Cl, N.

(−)-(2R,4R)-2-Fluoro-9-[(2-hydroxymethyl)-1,3-dioxolan-4-yl]adenine (28).

A solution of 16 (0.56 g, 1.12 mmol) in THF (20 mL) was treated with 1M n-$Bu_4NF$/THF (1.35 mL, 1.35 mmol) to furnish 22 (0.24 g, 85%) as a white crystalline solid, which was recrystallized from MeOH: UV ($H_2O$) $\lambda_{max}$ 260.8 nm (17,010), 268.5 (sh) nm (ε 13,510) (pH 7), 261.0 (16,390), 268.5 (sh) (ε 13,300) (pH2), 260.8 (ε 16,700), 268.5 (sh) (ε 13,200) (pH 11). Anal. ($C_9H_{10}FN_5O_3$) C, H, F, N.

(−)-(2R,4R)-9-[(2-Hydroxymethyl)-1,3-dioxolan-4-yl] guanine (25).

A mixture of 15 (0.29 g, 0.57 mmol), $HSCH_2CH_2OH$ (0.51 mL) and 1.0M NaOMe/MeOH (11.5 mL) in MeOH (20 mL) was refluxed for 3 hours. The reaction mixture was cooled and neutralized with glacial acetic acid. The solution was evaporated to dryness, and then the residue was triturated with $CHCl_3$, filtered and the filtrate was taken to dryness to give crude compound 19 (0.21 g, 75%), which without further purification was subjected to desilylation according to the same procedure described for 23 to give compound 25 (0.07 g, 61%) as a microcrystalline solid, which was recrystallized from MeOH: UV ($H_2O$) $\lambda_{max}$ 252.0 (ε 8,730) (pH 7), 254.4 (12,130), 277.5 (sh) (ε 8,070) (pH 2), 264.3 (ε10,800) (pH11). Anal. ($C_9H_{11}N_5O_4$) C, H, N.

(−)-(2R,4R)-2-Amino-9-[(2-hydroxymethyl)-1,3-dioxolan-4-yl]adenine (26).

A steel bomb was charged with compound 15 (0.28 g, 0.55 mmol), anhydrous ethanol (20 mL) saturated with $NH_3$, and heated at 90° C. for 6 hours. After cooling, the compound 20 (0.26 g, 95%) obtained on evaporated of the solvent in vacuo, and then desilylated according to the same procedure described for preparation of 23 to give 26 (0.10 g, 75%) as white micro needles, recrystallized from MeOH: UV ($H_2O$) $\lambda_{max}$ 279.0 nm (ε 8,040) (pH 7), 290.0 (ε 7,070) (pH2), 278.8 (ε 7,580) (pH11). Anal. ($C_9H_{12}N_6O_3$) C, H, N.

(−)-(2R,4R)-2-Amino-9-[(2-hydroxymethyl)-1,3-dioxolan-4-yl]purine can be prepared by reduction of compound 21 using a variety of reducing agents, including palladium on carbon and hydrogen gas or tributyltin hydride and azabisisobutyronitrile.

II. Anti-HIV Activity of Dioxolane Nucleosides

β-D-Dioxolane-nucleosides can be used as research tools to inhibit the growth of HIV in vitro, or can be administered to humans pharmaceutically to inhibit the growth of HIV in vivo.

The ability of β-D-dioxolane-nucleosides to inhibit HIV can be measured by various experimental techniques. The technique used herein, and described in detail below, measures the inhibition of viral replication in phytohemagglutinin (PHA) stimulated human peripheral blood mononuclear (PBM) cells infected with HIV-1 (strain LAV). The amount of virus produced is determined by measuring the virus-coded reverse transcriptase enzyme. The amount of enzyme produced is compared to an HIV control. The method is described in detail below.

Antiviral and Cytotoxic Assay in Human Peripheral Blood Mononuclear Cells.

A. Three-day-old phytohemagglutinin-stimulated PBM cells ($10^6$ cells/ml) from hepatitis B virus and HIV-1 seronegative healthy donors were infected with HIV-1 (strain LAV) at a concentration of about 100 times the 50% tissue culture infectious dose ($TICD_{50}$) per ml and cultured in the presence and absence of various concentrations of antiviral compounds.

B. Approximately 45 minutes after infection, the medium, with the compound to be tested (2 times the final concentration in medium) or without compound, was added to the flasks (5ml; final volume 10 ml). AZT was used as a positive control.

C. The cells were exposed to the virus (about $2 \times 10^5$ dpm/ml, as determined by reverse transcriptase assay) and then placed in a $CO_2$ incubator. HIV-1 (strain LAV) was obtained from the Center for Disease Control, Atlanta, Ga. The methods used for culturing the PBM cells, harvesting the virus and determining the reverse transcriptase activity were those described by McDougal et al. (*J. Immun. Meth.* 76, 171–183, 1985) and Spira et al. (*J. Clin. Meth.* 25, 97–99, 1987), except that fungizone was not included in the medium (see Schinazi, et al., *Antimicrob. Agents Chemother.* 32, 1784–1787 (1988)). The reverse transcriptase activity in the virus-infected control was about $2 \times 10^5$ dpm per ml. Blank and uninfected cell control values were about 300 and 1,000 dpm, respectively. Similar results are obtained when Step C is performed before step B.

D. On day 6, the cells and supernatant were transferred to a 15 ml tube and centrifuged at about 900 g for 10 minutes.

Five ml of supernatant were removed and the virus was concentrated by centrifugation at 40,000 rpm for 30 minutes (Beckman 70.1 Ti rotor). The solubilized virus pellet was processed for determination of the levels of reverse transcriptase. Results are expressed in dpm/ml of sampled supernatant.

The percent inhibition of virus, as determined from measurements of reverse transcriptase, is plotted versus the micromolar concentration of compound. The $EC_{50}$ is the concentration of compound at which there is a 50% inhibition of viral growth.

Using this assay, it has been discovered that a small number of β-D-dioxolanyl purine nucleosides are potent anti-HIV agents. Specifically, as indicated in Table 1, compounds 21, 25, and 26 exhibit a low effective median concentration, ranging from 0.027 to 0.69 μM.

TABLE 1

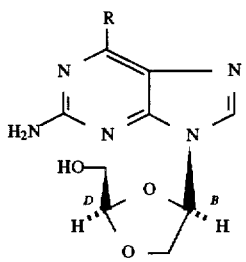

| R | Anomer | $EC_{50}$* |
|---|---|---|
| Cl | β-D | 0.9 |
| Cl | β-L | 13.4 |
| $NH_2$ | β-D | 0.7 |
| OH | β-D | 0.03 |

*Mean of at least 2 assays, using different donor cells. Standard error estimated at plus or minus 10%.

In contrast to the previous report that β-D-(±)-dioxolane-thymine has low efficacy against HIV in ATH8 cells, the enantiomerically pure β form 11 exhibited a potent anti-HIV activity ($EC_{50}$=0.3 μM). It was surprising to discover that enantiomerically pure β-D-(−)-dioxolane-T has significantly higher anti-HIV activity than the racemic mixture of the compound. This difference may be explained based on the rate of phosphorylation of 11 in these systems. As expected, the α-isomer 12 did not exhibit any significant anti-HIV activity. The $EC_{50}$ of (−)-1-[(2β,4β)-2-(hydroxymethyl)-4-dioxolanyl]thymine in PBM cells was measured as 0.2 μM.

III. Toxicity of Dioxolane Nucleosides

The toxicities of compounds 21, 25, and 26, were evaluated in uninfected human PBM cells, CEM cells (T-lymphoblastoid cell line obtained from ATCC, Rockville, Md) and Vero (African Green Monkey kidney) cells. The three compounds were not toxic in any of the cell lines at a concentration of 100 μM.

IV. Preparation of Pharmaceutical Compositions

Humans suffering from HIV infection can be treated by administering to the patient an effective amount of (−)-(2R,4R)-2-amino-6-chloro-9-[(2-hydroxymethyl)-1,3-dioxolan-4-yl]purine; (−)-(2R,4R)-9-[(-2-hydroxymethyl)-1,3-dioxolan-4-yl]guanine; (−)-(2R,4R)-2-amino-9-[(-2-hydroxymethyl)-1,3-dioxolan-4-yl]adenine; or (−)-(2R,4R)-2-amino-9-[(-2-hydroxymethyl)-1,3-dioxolan-4-yl]purine or a pharmaceutically acceptable derivative or salt thereof, optionally in a pharmaceutically acceptable carrier or diluent. The active materials can be administered by any appropriate route, for example, orally, parenterally, intravenously, intradermally, subcutaneously, or topically, in liquid or solid form.

The active compound is included in the pharmaceutically acceptable carrier or diluent in an amount sufficient to deliver to a patient a therapeutically effective amount without causing serious toxic effects in the patient treated.

A preferred dose of the active compound for all of the above-mentioned conditions will be in the range from about 1 to 60 mg/kg, preferably 1 to 20 mg/kg, of body weight per day, more generally 0.1 to about 100 mg per kilogram body weight of the recipient per day. The effective dosage range of the pharmaceutically acceptable derivatives can be calculated based on the weight of the parent nucleoside to be delivered. If the derivative exhibits activity in itself, the effective dosage can be estimated as above using the weight of the derivative, or by other means known to those skilled in the art.

The compound is conveniently administered in unit any suitable dosage form, including but not limited to one containing 7 to 3000 mg, preferably 70 to 1400 mg of active ingredient per unit dosage form. A oral dosage of 50–1000 mg is usually convenient.

Ideally the active ingredient should be administered to achieve peak plasma concentrations of the active compound of from about 0.2 to 70 μM, preferably about 1.0 to 10 μM. This may be achieved, for example, by the intravenous injection of a 0.1 to 5% solution of the active ingredient, optionally in saline, or administered as a bolus of the active ingredient.

The concentration of active compound in the drug composition will depend on absorption, inactivation, and excretion rates of the drug as well as other factors known to those of skill in the art. It is to be noted that dosage values will also vary with the severity of the condition to be 1s alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

A preferred mode of administration of the active compound is oral. Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

The active compound or pharmaceutically acceptable salt or derivative thereof can be administered as a component of an elixir, suspension, syrup, wafer, chewing gum or the like. A syrup may contain, in addition to the active compounds, sucrose as a sweetening agent and certain preservatives, dyes and colorings and flavors.

The active compound, or pharmaceutically acceptable derivative or salt thereof can also be mixed with other active materials that do not impair the desired action, or with materials that supplement the desired action, such as antibiotics, antifungals, antiinflammatories, or other antivirals, including other nucleoside anti-HIV compounds.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In a preferred embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc.

Liposomal suspensions (including liposomes targeted to infected cells with monoclonal antibodies to viral antigens) are also preferred as pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound or its monophosphate, diphosphate, and/or triphosphate derivatives are then introduced into the container. The container is then swirled by hand to free lipid material from the sides of the container and to disperse lipid aggregates, thereby forming the liposomal suspension.

V. Preparation of Phosphate Derivatives of β-D-Dioxolane-Nucleosides

Mono, di, and triphosphate derivative of β-D-dioxolane-nucleosides can be prepared as described below.

The monophosphate can be prepared according to the procedure of Imai et al., *J. Org. Chem.*, 34(6), 1547–1550 (June 1969). For example, about 100 mg of β-D-dioxolane-nucleoside and about 280 μl of phosphoryl chloride are reacted with stirring in about 8 ml of dry ethyl acetate at about 0° C. for about four hours. The reaction is quenched with ice. The aqueous phase is purified on an activated charcoal column, eluting with 5% ammonium hydroxide in a 1:1 mixture of ethanol and water. Evaporation of the eluant gives ammonium-(β-D-dioxolane-nucleoside)-5'-monophosphate.

The diphosphate can be prepared according to the procedure of Davisson et al., *J. Org. Chem.*, 52(9), 1794–1801 (1987). β-D-Dioxolane-nucleosides can be prepared from the corresponding tosylate, that can be prepared, for example, by reacting the nucleoside with tosyl chloride in pyridine at room temperature for about 24 hours, working up the product in the usual manner (e.g., by washing, drying, and crystallizing it).

The triphosphate can be prepared according to the procedure of Hoard et al., *J. Am. Chem. Soc.*, 87(8), 1785–1788 (1965). For example, β-D-dioxolane-nucleoside is activated (by making a imidazolide, according to methods known to those skilled in the art) and treating with tributyl ammonium pyrophosphate in DMF. The reaction gives primarily the triphosphate of the nucleoside, with some unreacted monophosphate and some diphosphate. Purification by anion exchange chromatography of a DEAE column is followed by isolation of the triphosphate, e.g., as the tetrasodium salt.

This invention has been described with reference to its preferred embodiments. Variations and modifications of the invention, enantiomerically pure β-D-dioxolane-nucleosides, will be obvious to those skilled in the art from the foregoing detailed description of the invention. It is intended that all of these variations and modifications be included within the scope of the appended claims.

We claim:

1. An enantiomerically pure β-D-dioxolanyl nucleoside of the structure:

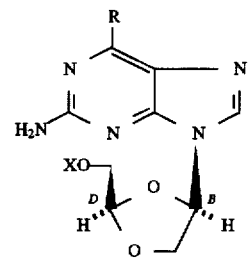

wherein R is OH, and X is selected from the group consisting of hydrogen, monophosphate, diphosphate, and triphosphate, or its pharmaceutically acceptable salt, and wherein the compound is at least 97% free of the corresponding β-L-enantiomer.

2. An enantiomerically pure β-D-dioxolanyl nucleoside of the structure:

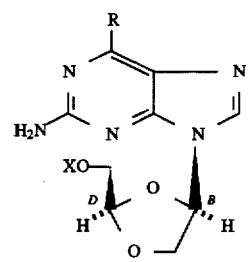

wherein R is $NH_2$, and X is selected from the group consisting of hydrogen, monophosphate, diphosphate, and triphosphate, or its pharmaceutically acceptable salt, and wherein the compound is at least 97% free of the corresponding β-L-enantiomer.

3. An enantiomerically pure β-D-dioxolanyl nucleoside of the structure:

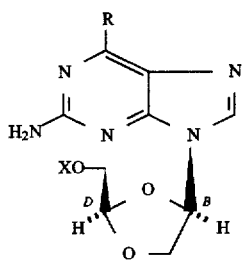

wherein R is H or Cl, and X is selected from the group consisting of hydrogen, monophosphate, diphosphate, and triphosphate, or a pharmaceutically acceptable salt thereof, and wherein the compound is at least 97% free of the corresponding β-L-enantiomer.

4. The compound of claim 1, wherein X is hydrogen.

5. The compound of claim 2, wherein X is hydrogen.

6. The compound of claim 3, wherein X is hydrogen.

7. (−)-(2R,4R)-9-[(-2-hydroxymethyl)-1,3-dioxolan-4-yl] guanine, which is at least 97% free of the corresponding β-L-enantiomer.

8. (−)-(2R,4R)-2-amino-9-[(2-hydroxymethyl)-1,3-dioxolan-4-yl]adenine, which is at least 97% free of the corresponding β-L-enantiomer.

9. (−)-(2R,4R)-2-amino-9-[(-2-hydroxymethyl)-1,3-dioxolan-4-yl]purine, which is at least 97% free of the corresponding β-L-enantiomer.

10. (−)-(2R,4R)-2-amino-6-chloro-9-[(2-hydroxymethyl)-1,3-dioxolan-4-yl]purine, which is at least 97% free of the corresponding β-L-enantiomer.

11. The compound of claim 1, wherein X is monophosphate.

12. The compound of claim 2, wherein X is monophosphate.

13. The compound of claim 3, wherein X is monophosphate.

* * * * *